United States Patent [19]

Yano

[11] Patent Number: 4,664,122
[45] Date of Patent: May 12, 1987

[54] ULTRASONIC TRANSDUCER ARRAY USED IN ULTRASONIC DIAGNOSIS APPARATUS

[75] Inventor: Masahiko Yano, Ootawara, Japan

[73] Assignee: Kabushiki Kaisha Toshiba, Kawasaki, Japan

[21] Appl. No.: 758,377

[22] Filed: Jul. 24, 1985

[30] Foreign Application Priority Data

Jul. 25, 1984 [JP] Japan ................. 59-153163

[51] Int. Cl.⁴ .............................................. A61B 10/00
[52] U.S. Cl. ..................... 128/660; 128/663
[58] Field of Search ............. 128/660, 661, 663; 73/625–626

[56] References Cited

U.S. PATENT DOCUMENTS

| 4,401,910 | 8/1983 | Beerman | 128/660 X |
| 4,470,305 | 9/1984 | O'Donnell | 128/660 X |
| 4,523,471 | 6/1985 | Lee | 73/626 |
| 4,566,459 | 1/1986 | Umemura et al. | 128/660 |

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

In an ultrasonic transducer array used in an ultrasonic diagnosis apparatus, the pitch of transducer elements of peripheral subarrays is made smaller than that of a central subarray. The central transducer elements are adapted for acquiring a tomogram of an object to be examined, and the peripheral transducer elements are adapted for acquiring flow rate information of the object, sound velocity information of tissue of the object or tomographic information using an electronic sector scan.

3 Claims, 8 Drawing Figures

FIG. 2
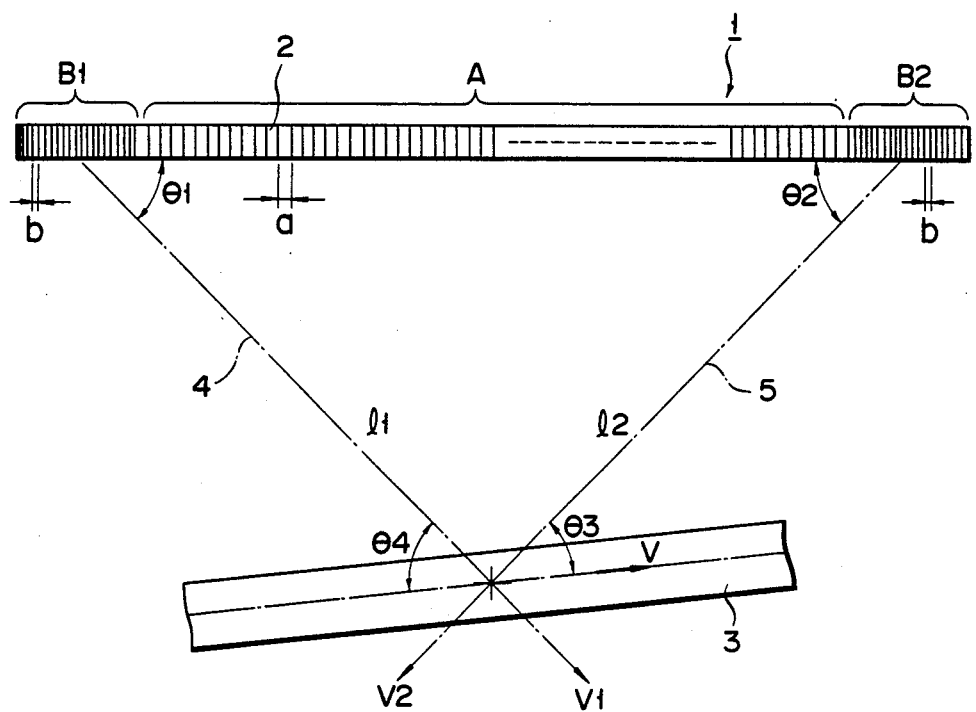
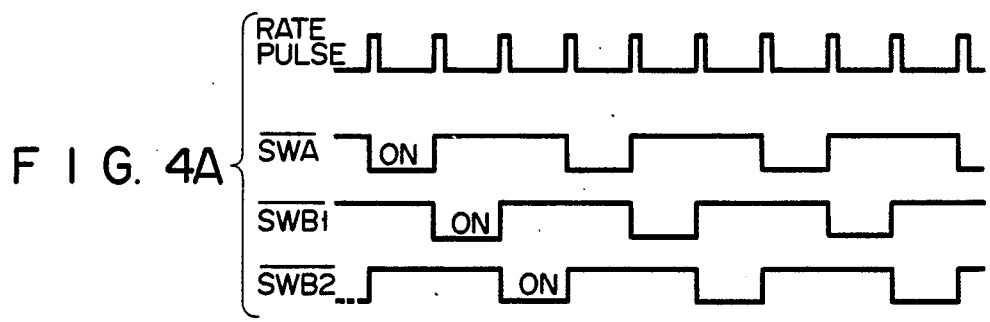
FIG. 4A
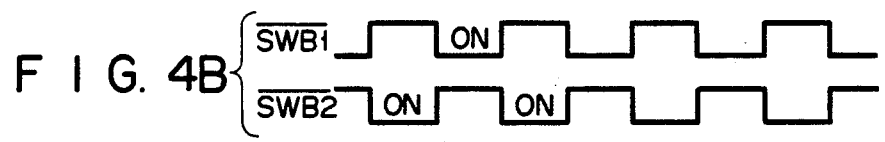
FIG. 4B

ULTRASONIC TRANSDUCER ARRAY USED IN ULTRASONIC DIAGNOSIS APPARATUS

BACKGROUND OF THE INVENTION

The present invention relates to an ultrasonic diagnosis apparatus and, more particularly, to an improvement of an ultrasonic transducer array used in an ultrasonic diagnosis apparatus.

In general, an ultrasonic wave is transmitted from a transducer array in an ultrasonic diagnosis apparatus to an object to be examined, and the transducer array receives echo signals from tissue of the object, thereby acquiring medical information. A B-mode image (i.e., a tomogram) of the object is most important. It is also often important to measure the flow rate of the blood of a patient for subsequent medical diagnosis. In a conventional method of measuring a blood flow, a frequency shift of echo signals of an ultrasonic wave transmitted from the ultrasonic transducer is detected based on the Doppler effect.

According to a first technique of the conventional blood flow measuring method, a Doppler ultrasonic beam is radiated to an object of interest from one direction, and the flow rate of blood is calculated in accordance with the frequency shift of the reflected ultrasonic beam. According to this technique, when the Doppler beam direction is not perpendicular to the blood flow, the resultant blood velocity VO must be corrected to obtain an actual flow rate V such that $V = VO \times \cos(\theta)$. For this reason, an angle $\theta$ formed by the Doppler beam direction and the blood flow direction must be measured on the screen of a TV monitor for displaying an ultrasonic tomogram.

According to a second technique, two ultrasonic probes are used. Two ultrasonic Doppler beams are radiated to the object of interest from two different directions. In this case, a mechanical means is indispensable to measure an angle formed by the two ultrasonic beams at the measuring point. In addition, a mechanical operation is also required to coincide one ultrasonic beam with the other at the measuring point. However, it is very difficult to cross the two Doppler beams on a plane including the measuring point. Since accurate coincidence of the two beams can be performed only with difficulty, blood flow measurement cannot be performed with high precision.

SUMMARY OF THE INVENTION

It is an object of the present invention to provide a new and improved ultrasonic transducer array suitable for various diagnostic purposes.

It is another object of the present invention to provide an ultrasonic transducer array for radiating an ultrasonic beam from an end thereof at a larger deflection angle as compared with an ultrasonic beam radiated from the center of the array.

It is still another object of the present invention to provide an ultrasonic transducer array for easily radiating two ultrasonic beams radiated from different directions at a point on a single plane.

It is a still further object of the present invention to provide an ultrasonic blood flow measuring apparatus which can be simply operated and which can acquire flow rate information of the blood of the object with high precision.

An ultrasonic transducer device used in an ultrasonic diagnosis apparatus of the present invention comprises an array of transducer elements each driven by a driving signal. The array has a central subarray and first and second peripheral subarrays. The pitch of the transducer elements in the first and second peripheral subarrays is smaller than in the central subarray.

Since the pitch of the transducer elements of the peripheral subarrays is smaller than that of the center subarray, deflection angles of the ultrasonic beams radiated from the peripheral subarrays can be increased. For this reason, the central subarray can be adapted for acquiring tomographic information in response to an electronic linear scan, and the peripheral subarrays can be adapted for acquiring blood flow information or sound velocity information in the tissue of the object. The subarrays can also be adapted for acquiring tomographic information in response to an electronic sector scan in additon to tomographic information from the central array responsive to the electronic linear scan.

BRIEF DESCRIPTON OF THE DRAWINGS

FIG. 2 is a diagram for explaining the relationship between the ultrasonic transducer array and blood flow measurement;

FIGS. 4A and 4B are respectively timing charts for explaining the operation of the ultrasonic diagnosis apparatus;

DETAILED DESCRIPTION OF THE PREFERRED EMBODIMENT

Figure 1:
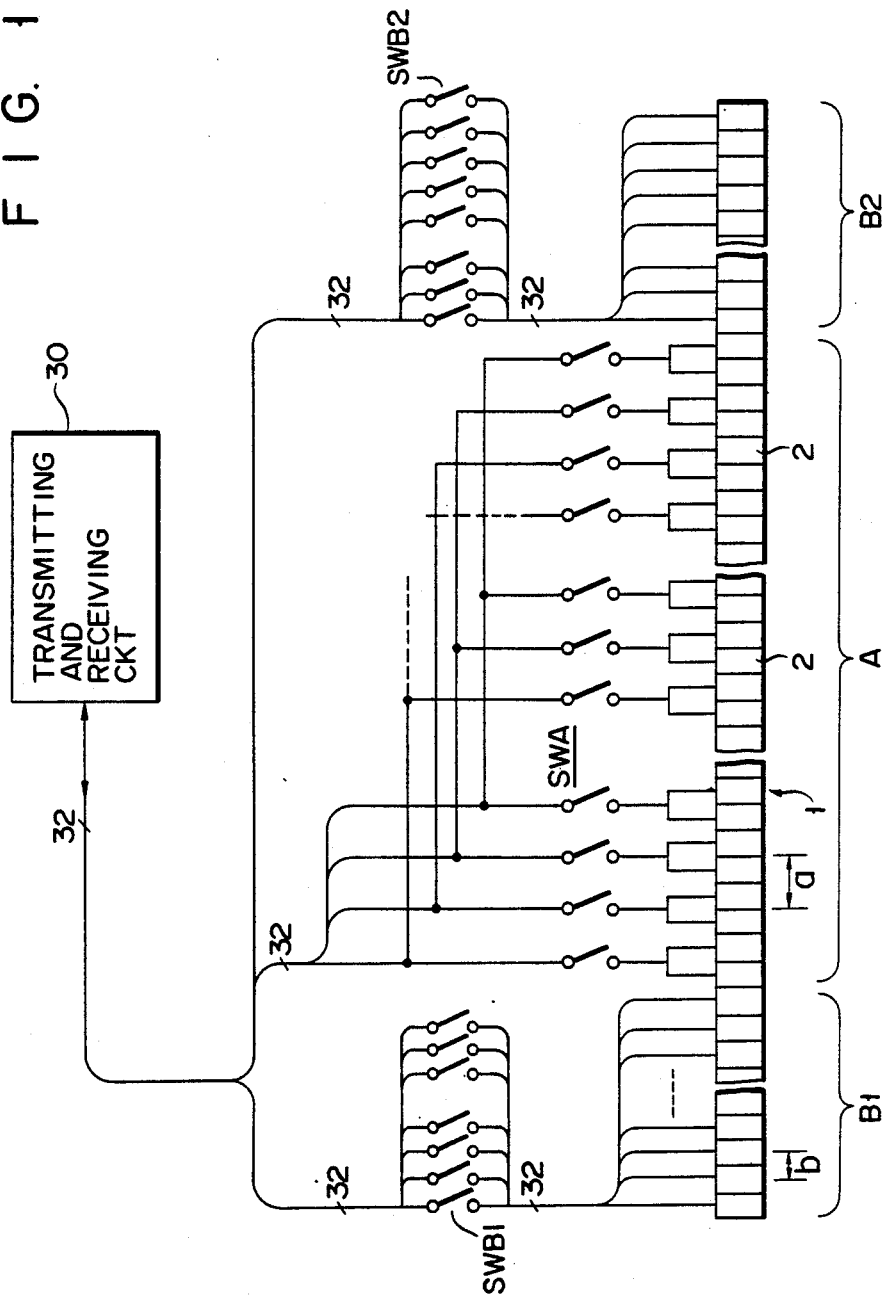
FIG. 1 is a diagram showing an ultrasonic transducer array and a driving arrangement thereof embodying the present invention.

Referring to FIG. 1, an ultrasonic transducer array 1 embodying the present invention comprises a number of ultrasonic transducer elements 2 arrayed to, in order to acquire a B mode image of an object to be examined, transmit/receive ultrasonic waves in response to an electronic linear scan as in the conventional ultrasonic transducer array. According to this invention the array 1 is arranged such that the pitch b of peripheral subarrays B1 and B2 is smaller than the pitch a of a central subarray A. This arrangement allows to obtain a tomogram of the object by the subarray A responsive to the electronic linear scan, and diagnostic information such as a blood flow by the subarrays B1 and B2.

The ultrasonic transducer array of the present invention can be manufactured by dicing a piezoelectric material such as ceramic in the same manner as in the conventional ultrasonic transducer array. The elements 2 of the ultrasonic transducer array can be formed at a constant pitch on a single plane. A plurality of adjacent elements (two in this embodiment) of the central subarray A are commonly driven as in a conventional transducer array. However, the elements 2 in the peripheral subarrays B1 and B2 are independently driven. Therefore, a set of two adjacent elements in the subarray A which are simultaneously driven and one element in the subarray B1 and B2 each serve as a one-channel element. Thus, the pitch of one-channel elements at the central portion is larger than that in the peripheral portion. The simultaneously driven elements in the central subarray A may comprise a few elements. By way of example, the subarray A has 96 channels (i.e., 192 elements), and the subarrays B1 and B2 each have 32 channels (32 elements). The pitch b of the subarray B1 or B2 is on the order of 0.24 mm.

As shown in FIG. 1, the transducer elements of the subarrays B1 and B2 are coupled to a transmitting and receiving circuit 30 through corresponding switch circuits SWB1 and SWB2 each having 32 switching elements. The 96 channel elements of the subarray A are connected to a switch circuit SWA having 96 switching elements. As is well known, three-channel elements are commonly connected on the output side of the switch circuit SWA, thereby forming 32 input (output) channels associated with the central elements. 32-channel signal transmission lines coupled to the subarrays A, B1 and B2 are selectively coupled to the transmitting and receiving circuit 30.

The elements 2 of the subarrays A, B1 and B2 of the ultrasonic transducer array may be subjected to an electronical linear scan in a conventional manner to obtain a tomogram of the object which includes blood vessels 3. As shown in FIG. 2, since the element pitch per channel in the subarrays B1 and B2 is smaller than that in the central subarray A, ultrasonic beams 4 and 5 can be transmitted at large deflection angles $\theta 1$ and $\theta 2$ by delay-driving the peripheral transducer elements. The beams 4 and 5 are used as ultrasonic Doppler beams for measuring a blood flow rate. In this manner, the ultrasonic probe of the present invention can acquire a normal B mode image. In addition, since the Doppler beams are transmitted from the peripheral subarrays, these beams can be intersected at a measuring point on a single plane.

Figure 3:
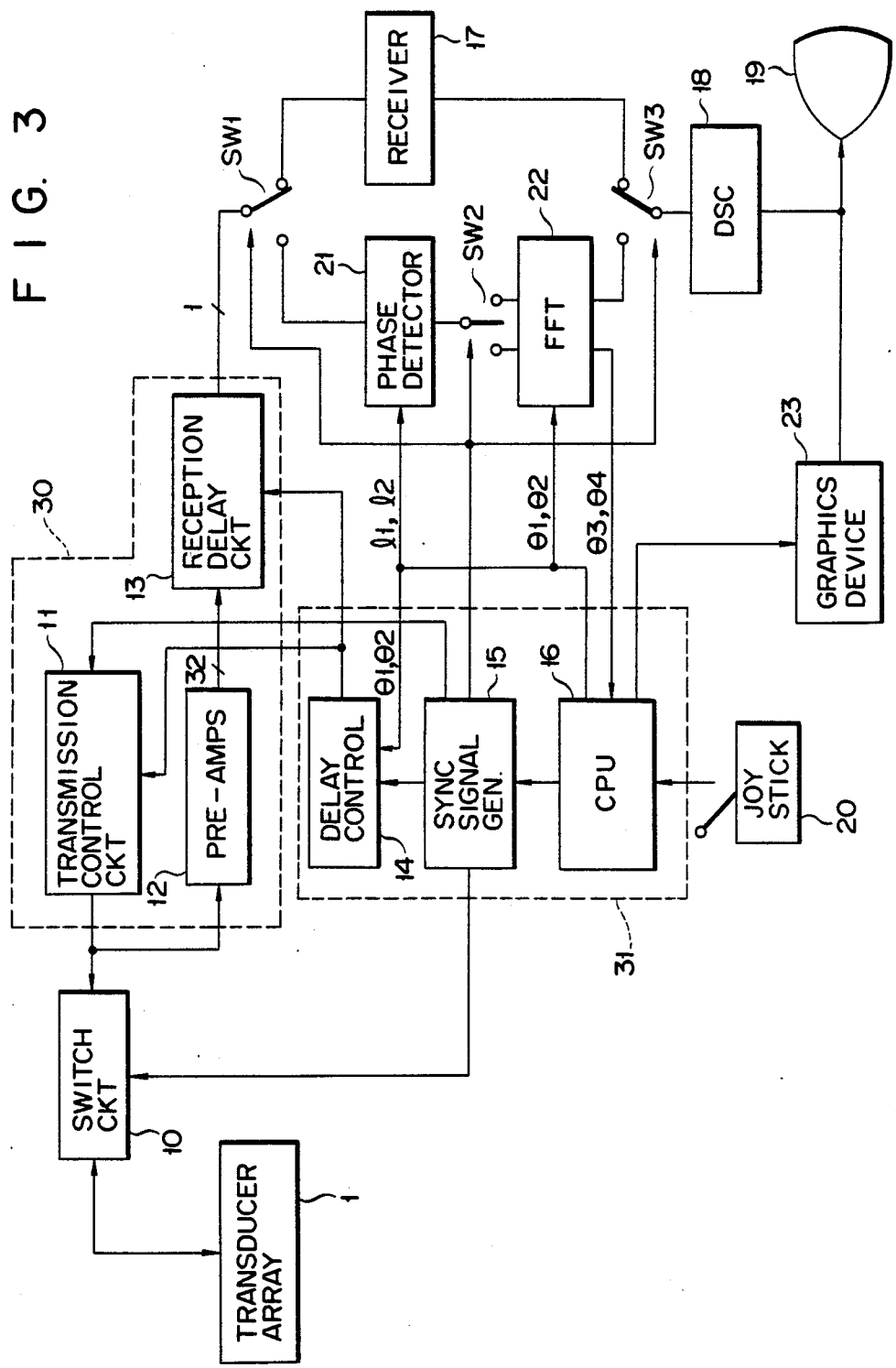
FIG. 3 is a block diagram of an ultrasonic diagnosis apparatus using the ultrasonic transducer of the present invention so as to acquire blood flow information and a tomogram of an object.

An ultrasonic diagnosis apparatus using the ultrasonic transducer will be described with reference to FIG. 3. This ultrasonic diagnosis apparatus has a function of visually displaying a tomogram (i.e., the B mode image) of the object on a display 19 and a function of displaying a blood flow pattern waveform at a measuring point designated on the B mode image.

The arrangement for displaying the B mode image will be described. A switch circuit 10 comprises the switch circuits SWA, SWB1 and SWB2 described above, and applies drive signals to the transducer array 1 from the transmission/reception circuit 30 to scan the transducer elements in response to a control circuit 31. The circuit 30 comprises a transmission control circuit 11, a preamplifier (pre-amps) 12, and a reception delay circuit 13. The circuit 11 comprises a pulser and delay elements to supply properly delayed drive pulses to the array 1 through the circuit 10. The preamplifier 12 amplifies echo signals received by the array 1. The delay circuit 13 processes 32-channel echo signals from the preamplifier 12, which are variously delayed in time, for the purpose of reception focusing. More specifically, the delayed echo signals are delayed to be in phase, and the in-phase echo signals are added together.

The control circuit 31 comprises a delay control circuit 14, a sync signal generator 15 and a central processing unit (CPU) 16. The delay control circuit 14 supplies delay control data to the circuits 11 and 13 to control the delay times of the drive signals and the received echo signals. The generator 15 controls the scanning timings of the transducer elements by the switch circuit 10 and operates switches SW1, SW2 and SW3 (to be described later) in accordance with a transducer array operating mode (i.e., the tomogram mode or the blood flow mode). The CPU 16 controls the entire operation of the apparatus.

Figure 5:
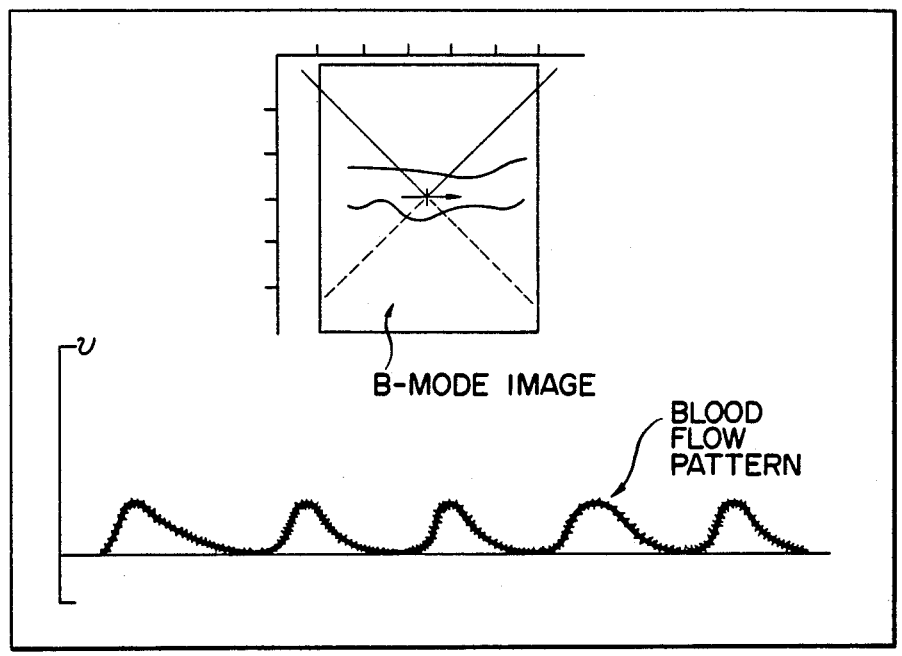
FIG. 5 is a diagram showing the tomogram and blood flow information which are displayed on a display device of the apparatus of FIG. 3.

An output of the circuit 13 is coupled to a receiver 17 through the switch SW1. An output of the receiver 17 is coupled to a digital scan converter (DSC) 18 through the switch SW3. A tomogram signal demodulated by the receiver 17 is stored in a first memory area of a frame memory of DSC 18. The tomogram signal read out from the frame memory is supplied to the display 19 so as to visually display a tomogram image of the object on a first display area of the display, as shown in FIG. 5.

The arrangement for acquiring blood flow information will next be described. A joystick 20 is provided to designate a measuring point for blood flow. The joystick 20 is operated by an operator to designate, through CPU 16 and a graphics device 23, a point of the blood vessel 3 in the tomogram image displayed on the display 19. As a result, position data on the measuring point is input to CPU 16. The CPU 16 calculates the deflection angles $\theta 1$ and $\theta 2$ of beams 4 and 5 radiated from the subarrays B1 and B2 of the transducer array 1, and the distances l1 and l2 between the centers of arrays B1 and B2 and the measuring point in accordance with the input position data of the measuring point.

The deflection angle data of Doppler beams 4 and 5 are input to the delay control circuit 14. The control circuit 14 applies delay control data to the transmission control circuit 11 to control delay times of the drive pulses for driving the peripheral transducer elements so as to intersect the beams 4 and 5 at the measuring point. At the same time, the control curcuit 14 supplies delay control data to the reception delay circuit 13 so as to process the received echo signals. The sync signal generator 15 controls the switch circuit 10 so as to alternately drive the subarrays B1 and B2 so that the Doppler beams 4 and 5 having an identical frequency are alternately radiated. The transducer elements of the subarrays B1 and B2 alternately receive corresponding echo signals. Referring to FIG. 2, the echo signals of the ultrasonic beams 4 radiated from the transducer elements of the subarray B1 are received by the elements thereof. Similarly, the echo signals of the ultrasonic beam 5 emitted from the subarray B2 are received by the elements thereof.

The received echo signals are supplied to a phase detector 21 through the preamplifier 12, the delay circuit 13 and the switch SW1. The detector 21 samples the channel echo signals from the circuit 13 in response to data (data concerning a predetermined period of time from the Doppler beam radiation to reception of a corresponding echo signal) associated with measuring distances l1 and l2 and supplied from CPU 16. An output signal of the detector 21 is coupled to one of two inputs of a fast Fourier transformer (FFT) 22 so as to independently analyze received echo signals of the Doppler beams 4 and 5.

The FFT 22 calculates frequency shifts of the echo signals corresponding to the Doppler beams 4 and 5 in accordance with output signals of the detector 21. The FFT calculates the velocities V1 and V2 of beams 4 and 5 in the directions of radiation in accordance with the frequency shifts. Thereafter, FFT 22 calculates intersection angles $\theta 3$ and $\theta 4$ (FIG. 2) between beams 4 and 5 and the blood vessel 3 using the velocities V1 and V2 and the deflection angles $\theta 1$ and $\theta 2$ provided by CPU 16 as follows:

$$\theta 3 = \arctan\ [V2/\{V1\cdot\sin\ (\theta 1+\theta 2)\} - \tan\ (\theta 1+\theta 2)] \quad (1)$$

$$\theta 4 = \arctan\ [V1/\{V2\cdot\sin\ (\theta 1+\theta 2)\} - \tan\ (\theta 1+\theta 2)] \quad (2)$$

The FFT 22 calculates blood flow information (i.e., a Doppler pattern representing frequency shifts) v on the basis of one of $\theta 3$ and $\theta 4$ as follows:

$$v = V1\cdot\cos\ (\theta 4) \quad (3)$$

$$v = V2\cdot\cos\ (\theta 3) \quad (4)$$

The blood flow information v is given in the form of a waveform whose amplitude varies from instant to instant. The FFT 2 may be arranged to provide output blood flow information v in accordance with an average value of blood flow data obtained by equations (3) and (4). The blood flow information v obtained by FFT 2 is stored in a second memory area of the frame memory of DSC 18 through switch SW3. The blood flow pattern information v read out from DSC 18 is visually displayed on a second display area of display 19, as shown in FIG. 5.

Data concerning the angles $\theta 1$, $\theta 2$, $\theta 3$ and $\theta 4$ and the measuring distances l1 and l2 are supplied to graphics device 23 so that, as shown in FIG. 5, the Doppler beams 4, 5, an intersection of beams 4 and 5 and an arrow indicating the blood flow direction are pictorially displayed on the tomogram image, as shown in FIG. 5.

The operation of the ultrasonic diagnosis apparatus as described above will be described with reference to timing charts of FIGS. 4A and 4B. The ultrasonic diagnosis apparatus can be operated to simultaneously acquire tomogram and blood flow information of the object, or to acquire only the tomogram or the blood flow information.

FIG. 4A is a timing chart for acquiring a tomogram and blood flow information on a real time basis. The sync signal generator 15 sequentially enables switch circuits SWB1, SWA and SWB2 in synchronism with rate pulses generated therein. During an enable period of each switch circuit, a plurality of switching elements in the switch circuit are sequentially turned on. The transmission control circuit 11 supplies drive pulses to transducer elements of array 1 through switch circuit 10 in response to sync signal generator 15. When the elements of subarray B1 of array 1 are excited, the ultrasonic beam 4 is radiated and its echo signals are received by the same elements. The generator 15 causes switch SW1 to couple the output of delay circuit 13 to phase detector 21 and causes switch SW2 to couple the output of detector 21 to an input of FFT 22 for Doppler beam 4. At the same time, the generator 15 causes switch SW3 to couple the output of FFT 22 to DSC 18.

During an enable period of switch circuit SWA, the elements of subarray A are excited to scan a region of interest of the object. The switch SWA selects 32 adjacent channel elements. The generator 15 causes switch SW1 to couple the output of delay circuit 13 to receiver 17 and causes switch SW3 to couple the output of receiver 17 to DSC 18. At next period, the switch SWA shifts the 32 adjacent channel elements by one channel element. As a result of such a linear scanning, tomographic information is stored in DSC 18, and a tomogram image is displayed on display 19.

During an enable period of switch circuit SWB2, the elements of subarray B2 of array 1 are excited to radiate Doppler beam 5. The corresponding echo signals are received by the same elements. During this period, the generator 15 causes switch SW1 to couple the output of circuit 13 to detector 21 and switch SW2 to couple the output of detector 21 to the input of FFT 22 corresponding to the beam 5. The generator 15 causes switch SW3 to couple the output of FFT 22 to DSC 18. As a result, the blood flow information at the measuring point on the blood vessel in the tomogram is displayed together with the tomogram on display 19. The beams 4 and 5 and the intersection thereof are pictorially displayed on the tomogram, so that the operator may use joystick 20 to arbitrarily set a measuring point. It should be noted that the beams 4 and 5 are deflected at large angles since the pitch of the elements of subarrays B1 and B2 of transducer array 1 is smaller than that of subarray A. Furthermore, since the transducer elements for radiating beams 4 and 5 are formed on the same plane, a special operation to intersect beams 4 and 5 at the measuring point can be omitted.

FIG. 4B is a timing chart for obtaining only blood flow information. In order to acquire the blood flow information only, the generator 15 is only required to alternately enable switch circuits SWB1 and SWB2, as is apparent from the timing chart. In order to acquire only tomographic information, the generator 15 is required to enable only switch circuit SWA.

Figure 6:
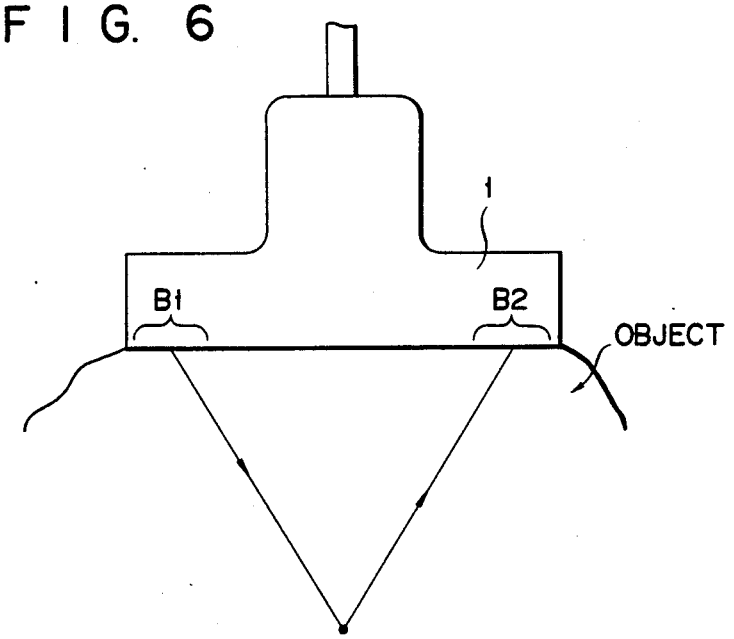
FIG. 6 is a diagram for explaining measurement of sound velocity in an object by using the ultrasonic transducer array of the present invention.

The transducer array of the present invention may be applied not only to measurement utilizing the Doppler effect, but also to other applications. FIG. 6 shows an application of sound velocity measurement in tissue of the object. In this case, an ultrasonic beam is radiated from the peripheral subarray B1 of array 1, and the beam reflected by the tissue which crosses it is received by the other peripheral subarray B2. A time measuring circuit (not shown) is provided in stead of the phase detector 21 and FFT 22 and measures a propagation time from the subarray B1 to the subarray B2. A computing circuit (not shown) computes sound velocity of the tissue along the crossed beams by a geometrical relation. More detailed techniques are disclosed in co-pending U.S. patent application Ser. No. 737,472 filed May 24, 1985; entitled "SYSTEM AND METHOD FOR MEASURING SOUND VELOCITY OF TISSUE IN AN OBJECT BEING INVESTIGATED"; and assigned to the same assignee as the present application.

Figure 7:
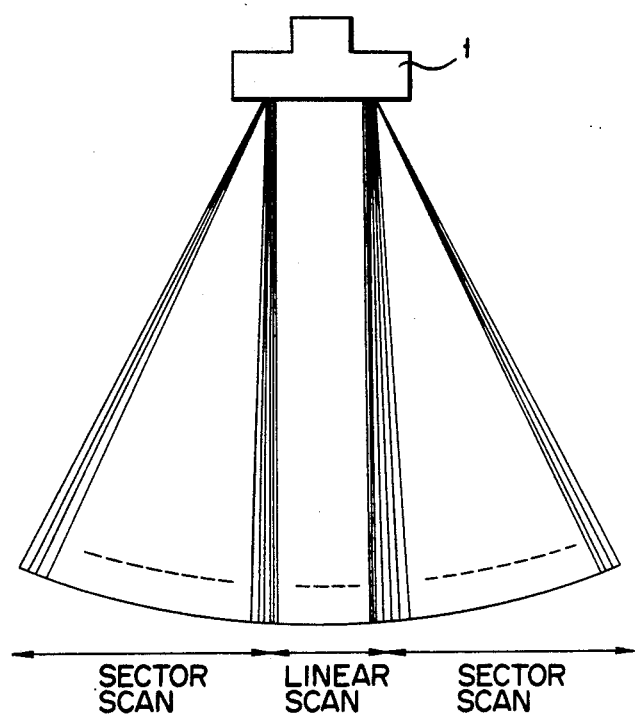
FIG. 7 is a diagram for explaining linear and sector scans using the ultrasonic transducer array of the present invention.

FIG. 7 shows another application of the transducer array of the present invention. According to this invention, an ultrasonic beam radiated from the peripheral portion of the transducer array can be steered at a larger deflection angle than at the central portion of the array. With this property of the transducer array the central subarray A of array 1 may be adapted for the linear scan of the object, and the peripheral subarrays B1 and B2 may be adapted for the sector scan. First, the switch circuit 10 selects the subarray B1. The transmission control circuit 11 and the reception circuit 13 perform the beam steering from left hand until 0 degree in FIG. 7. Second, the switch circuit 10 successively selects a group of elements in the subarray A to shift the beams from left hand until the end of the subarray A. Third, the circuit 10 selects the subarray B2, the circuits 11 and 13 perform the beam steering from 0 degree until a certain degree of right hand. In this operation a trapezoidal scanning area can be provided. It may apply to the above embodiments. Since the pitch at the subarrays is smaller than that of the central subarray, a side lobe of the ultrasonic radiation pattern at the peripheral portions can be decreased.

What is claimed is:

1. An ultrasonic scanning apparatus for imaging a subject to obtain tomogram signals and for obtaining absolute blood flow information concerning said subject, said apparatus comprising:
   an ultrasonic transducer array having a plurality of independently driven channel elements arranged in a row, said transducer array having first, second and third subarrays, said second subarray being disposed between said first and third subarrays, and each of said channel elements having a pitch such that pitch of said channel elements in said first and third subarrays is smaller than the pitch of said channel elements in said second subarray;
   first drive means for driving said first and third subarrays to alternately steer first and second ultrasonic beams generated from said first and third subarrays, respectively, in different directions such that said first and second beams intersect at said blood vessel, said first drive means including means for exciting the channel elements in said first and third subarrays at different delay times and for receiving signals representative of said beams after reflection;
   second drive means for driving said second subarray to generate a third ultrasonic beam to scan said object in a linear fashion;
   Doppler processing means for detecting two different Doppler signals from said received signals thereby to obtain said absolute blood flow information independent of said steered directions of said first and second ultrasonic beams;
   receiving means for processing tomogram signals obtained from said third ultrasonic beam to produce a tomogram; and
   display means connected to said Doppler processing means and said receiving means for displaying said tomogram and said absolute blood flow information.

2. The apparatus according to claim 1, further including means for driving said first and second drive means alternately.

3. The apparatus according to claim 2, further comprising switching means coupled to said first and second drive means and to said first, second, and third subarrays for alternately selecting said first, second and third subarrays.

* * * * *